US00PP08617P

United States Patent [19]

Kordes

[11] Patent Number: Plant 8,617

[45] Date of Patent: Mar. 1, 1994

[54] ROSE PLANT KORBACOL

[75] Inventor: Wilhelm Kordes, Sparrieshoop, Fed. Rep. of Germany

[73] Assignee: Bear Creek Gardens, Inc., Medford, Oreg.

[21] Appl. No.: 38,150

[22] Filed: Mar. 29, 1993

[51] Int. Cl.[5] ..... A01H 5/00

[52] U.S. Cl. ..... Plt./15

[58] Field of Search ..... Plt. 15

*Primary Examiner*—James R. Feyrer
*Assistant Examiner*—Bruce R. Campell
*Attorney, Agent, or Firm*—Klarquist, Sparkman, Campbell, Leigh and Whinston

[57] ABSTRACT

Hybrid Tea Rose having vigorous, upright growth; large, bright yellow flowers; intense, fruit-like fragrance; dark green, leathery foliage; and small thorns on stems.

1 Drawing Sheet

The present invention relates to a new and distinct variety of rose plant of the Hybrid Tea class which was originated by me by crossing an unnamed seedling with the variety Cocktail 80 (unpatented).

The primary objective of this breeding was to produce a new rose variety having the yellow flower color of the male parent but with the improved vigor and production of the female parent. The objective was substantially achieved along with other desirable improvements as evidenced by the following unique combination of characteristics which are outstanding in the new variety and which distinguish it from its parents, as well as from all other varieties of which I am aware:

1. A very strong, fruit-like fragrance;
2. Very leathery, glossy, green foliage;
3. Bright yellow flower color;
4. Many small thorns on stems; and
5. Very vigorous, upright growth.

Asexual reproduction of this new variety by budding, as performed at Wasco, Calif., and Sparrieshoop, Germany, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:
- *Seed parent.*—An unnamed seedling.
- *Pollen parent.*—Cocktail 80 (unpatented).

Classification:
- *Botanical.*—*Rosa hybrida.*
- *Commercial.*—Hybrid Tea.

FLOWER

Observations made from specimens grown in a greenhouse environment in Somis, Calif., and Sparrieshop, Germany, from March through October, 1992.

Blooming habit: Recurrent.

Bud:
- *Size.*—1½ inches when the petals start to unfurl.
- *Form.*—Long, pointed ovoid.
- *Color.*—When sepals first divide, bud color is Yellow Group 13A. When half blown, the upper and lower sides of the petals are Yellow Group 13A.
- *Sepals.*—Color: Green Group 138B. Surface texture: Covered in fine hairs. There are three normally to heavily appendaged sepals. There are two unappendaged sepals with hairy edges.
- *Receptacle.*—Color: Green Group 137D. Shape: Funnel. Size: Medium. Surface: Smooth.
- *Peduncle.*—Length: Medium (3-3¼ inches). Surface: Smooth. Color: Medium green. Strength: Stiff, erect.

Bloom:
- *Size.*—Large. Average open size is 4½-5 inches.
- *Borne.*—Singly.
- *Stems.*—Long (22-26 inches).
- *Form.*—When first open: High centered. Permanence: Flattens; all petals curl.
- *Petalage.*—Number of petals under normal conditions: 35-40.
- *Color.*—The upper and lower sides of the petals are Yellow Group 13A with fading in bright sunlight in a greenhouse to Yellow Group 13D. The base of each petal is Yellow Group 13A. The major color on the upper side is Yellow Group 13A.
- *Variegations.*—None.
- *Discoloration.*—The general tonality at the end of the first day: No change. At the end of the third day: Fading at the petal margins from Yellow Group 13A to Yellow Group 13D.
- *Fragrance.*—Strong, fruit-like fragrance.

Petals:
- *Texture.*—Thick.
- *Shape.*—Round.
- *Form.*—Tips slightly recurved, edges slightly quilled.
- *Arrangement.*—Imbricated, with few petaloids in the center.
- *Persistance.*—Drop off cleanly.
- *Lastingness.*—On the plant: Long (5-6 days). As a cut flower: Long (7-8 days).

Reproductive parts:

*Anthers.*—Size: Medium. Quantity: Many. Color: Yellow. Arrangement: Regular around styles, mixed with occasional petaloids.

*Filaments.*—Color: White.

*Pollen.*—Color: Lemon yellow.

*Styles.*—Color: Yellow.

*Stigmas.*—Color: Yellow.

Form: Bush.

Growth: Very vigorous, upright, branching.

Foliage:

*Number of leaflets on normal mid-stem leaves.*—5, or occasionally 7.

*Size.*—Large (7×6 inches).

*Quantity.*—Abundant.

*Color.*—New foliage: Greenish red. Old foliage: Dark green.

Leaflets:

*Shape.*—Broadly oval.

*Texture.*—Upper side: Leathery, glossy.

*Edge.*—Serrated.

*Serration.*—Single, small.

*Petiole rachis.*—Color: Green.

*Petiole underside.*—Smooth, with occasional prickles.

*Stipules.*—Medium, serrated, bearded.

*Disease resistance.*—Susceptible to mildew under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Short, hooked downward.

*Color when young.*—Transparent.

Small prickles:

*Quantity.*—On main stalks: Many. On laterals: Many.

*Color.*—Transparent.

I claim:

1. A new and distinct variety of rose plant of the Hybrid Tea class, substantially as herein shown and described, characterized particularly as to novelty by the unique combination of its vigorous, upright growth; its large, bright yellow flower; its intense, fruit-like flower fragrance; its dark green, leathery foliage; and the presence of small thorns on stems.

* * * * *

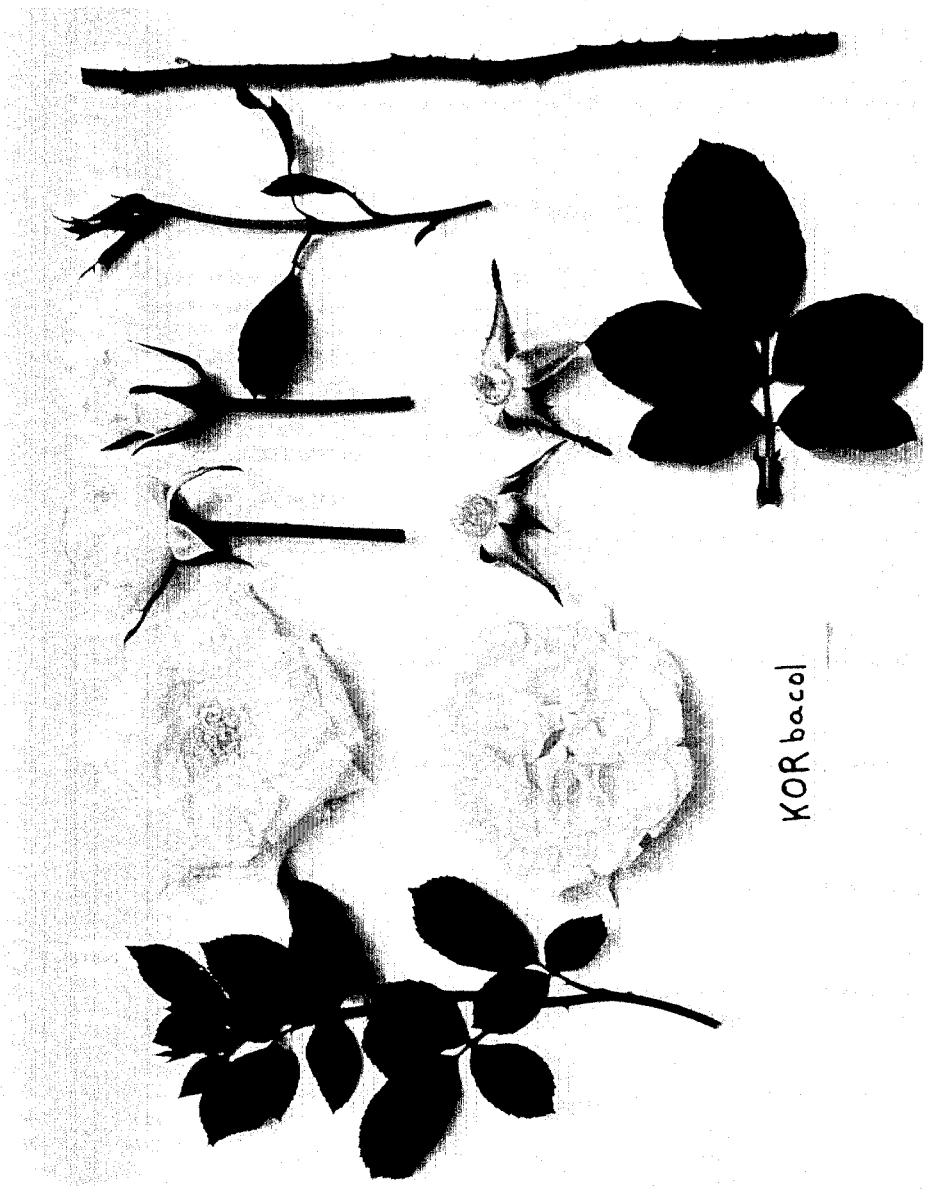
KOR bacol